United States Patent
Ralph et al.

(10) Patent No.: US 8,343,162 B2
(45) Date of Patent: ***Jan. 1, 2013

(54) DISTRACTION INSTRUMENT FOR USE IN ANTERIOR CERVICAL FIXATION SURGERY

(75) Inventors: James D. Ralph, Seaside Park, NJ (US); Thomas N. Troxell, Pottstown, PA (US)

(73) Assignee: SpineCore, Inc., Allendale, NJ (US)

( * ) Notice: Subject to any disclaimer, the term of this patent is extended or adjusted under 35 U.S.C. 154(b) by 1135 days.

This patent is subject to a terminal disclaimer.

(21) Appl. No.: 11/982,805

(22) Filed: Nov. 5, 2007

(65) Prior Publication Data
US 2008/0065095 A1   Mar. 13, 2008

Related U.S. Application Data

(63) Continuation of application No. 10/725,306, filed on Dec. 1, 2003, now Pat. No. 7,316,685, which is a continuation of application No. 10/003,000, filed on Nov. 30, 2001, now Pat. No. 6,669,699.

(51) Int. Cl.
*A61B 17/66* (2006.01)
(52) U.S. Cl. .................... 606/90; 606/198; 606/248
(58) Field of Classification Search .......... 606/57, 606/58, 90, 191–193, 198, 279, 248, 249; 623/17.11, 17.15, 17.16
See application file for complete search history.

(56) References Cited

U.S. PATENT DOCUMENTS

| | | | | |
|---|---|---|---|---|
| 5,390,683 A * | 2/1995 | Pisharodi | .............. | 128/898 |
| 5,653,763 A * | 8/1997 | Errico et al. | .............. | 623/17.11 |
| 6,436,119 B1 * | 8/2002 | Erb et al. | .............. | 606/198 |
| 6,669,699 B2 * | 12/2003 | Ralph et al. | .............. | 606/90 |
| 6,821,298 B1 * | 11/2004 | Jackson | .............. | 623/17.15 |
| 7,316,685 B2 * | 1/2008 | Ralph et al. | .............. | 606/90 |

* cited by examiner

*Primary Examiner* — Kathleen Sonnett
(74) *Attorney, Agent, or Firm* — Lerner, David, Littenberg, Krumholz & Mentlik, LLP

(57) ABSTRACT

An intervertebral distraction tool has a clamshell head with upper and lower halves, each having a curvate outer surface and a flat inner surface. The distal side of the head is hinged so that the head opens and closes from the proximal side of the head. The hinge is a separating hinge that allows the halves to not only angulate with respect to one another about the hinge axis, but also to vertically separate from one another at the hinge. A distraction separator has decreasing taper at its distal end and a longitudinal bore that accommodates the elongate shaft of the trial so that the separator can be moved longitudinally relative to the shaft. Upon forward movement of the separator, the tapered upper and lower surfaces engage the flat inner surfaces of the head, causing the halves to angulate about the hinge axis of the head, thereby opening the head.

18 Claims, 4 Drawing Sheets

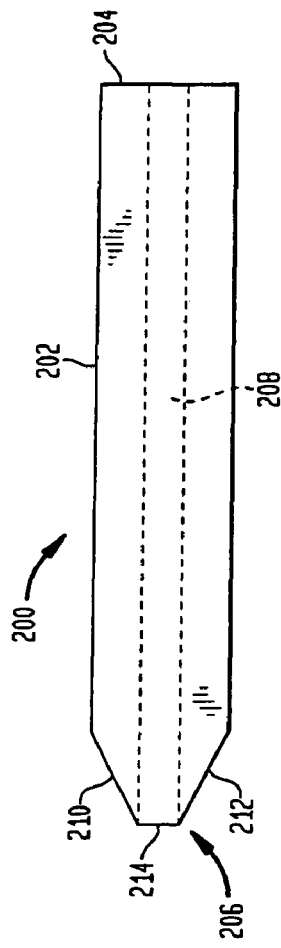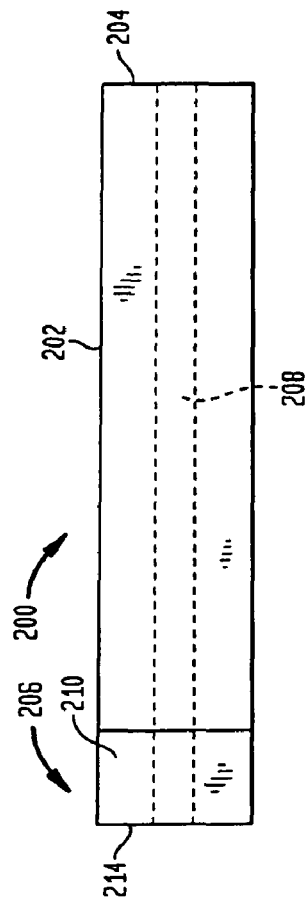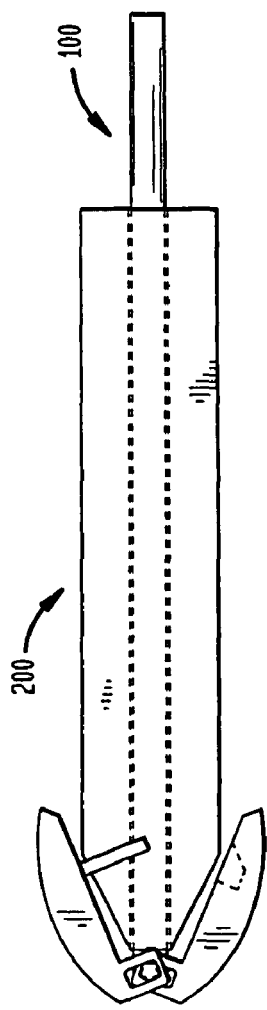

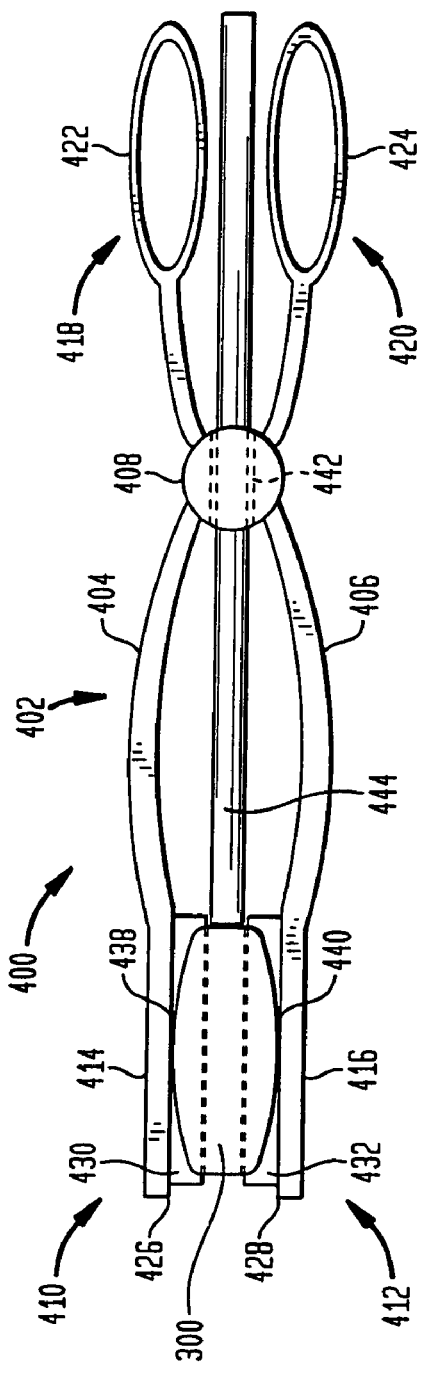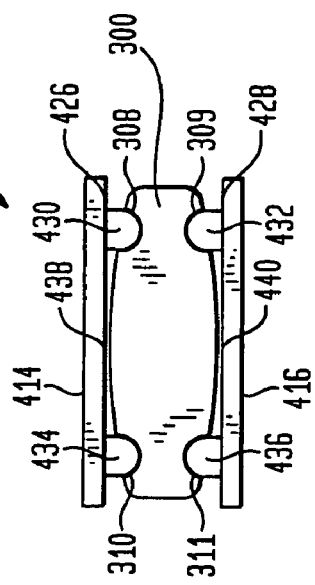
FIG. 4A
FIG. 4B

DISTRACTION INSTRUMENT FOR USE IN ANTERIOR CERVICAL FIXATION SURGERY

CROSS-REFERENCE TO RELATED APPLICATIONS

This application is a continuation of U.S. application Ser. No. 10/725,306 (now U.S. Pat. No. 7,316,685), filed on Dec. 1, 2003, which is a continuation of U.S. application Ser. No. 10/003,000, filed on Nov. 30, 2001, now U.S. Pat. No. 6,669,699, which are incorporated herein by reference.

BACKGROUND OF THE INVENTION

This invention relates generally to a medical instrument for use in anterior cervical spine surgery and more specifically to a distraction instrument used in the treatment and correction of pathologies in the cervical spine.

The spinal column consists of more than 20 discrete bones which are joined together in a highly complex arrangement which houses and protects critical elements of the nervous system and serves as a structural framework around which there are innumerable peripheral nerves and circulatory bodies in close proximity. In spite of these complicating features, the spine is a highly flexible structure, capable of a high degree of curvature and twist in nearly every direction permitting human beings a high degree of physical dexterity. In general these bones are coupled sequentially to one another by tri-joint complexes which consists of an anterior intervertebral disc and the two posterior facet joints. The anterior intervertebral discs of adjacent bones are cushioning cartilage spacers.

The bones and connective tissue of the neck, or cervical spine, are particularly complex in that they are smaller, are the most flexible in the spinal column, and are adjacent to the most critical circulatory, respiratory, and digestive tissues in the body. Long term degeneration of the cartilage spacers and/or trauma, can cause adjacent bones of the cervical spine to collapse together and/or become axially displaced (that is, become segmentally offset). These and other failure modes can cause significant pain as well as catastrophic neurological problems.

The traditional course of surgical treatment can include the implantation of a plate which seats against the anterior surfaces of adjacent bones, and the fixation of the plate thereto with bone screws immobilizes the two bones in the distracted and aligned position.

Concerns for the overall safety of this method of treatment, however, include the risk of screw pull out and/or breakage, or plate breakage, each of which are accompanied by the severe risk of esophegeal perforation, which can be fatal if not treated immediately and aggressively. The surgical effectiveness of this treatment is enhanced dramatically if the adjacent bones are able to fuse together across the distracted space, thus forming a single bony element which can support the neck without needing to load the metal plate (thus risking breakage or other failure mode). The problem is that the distraction increases the distance between the fusing bones, and the need to create the bone bridge requires that the bones be close enough to grow together. These competing factors have made the use of porous material as a spacer material desirable. This spacer physically braces the bones at the desired positions, permitting the bones to fuse across the entire assembly.

Similar techniques have been employed in other spinal infirmities, including collapsed disc spaces in the thoraco-lumbar regions of the spine. The present invention is therefore applicable to the treatment of any spinal disorder in which the space between vertebral bones needs to be surgically separated (the bones distracted), and then fused to one another, however, for the purposes of this invention disclosure, only the application to the cervical spine shall be described hereinbelow.

Before the implant may be inserted into the space, however, the height of the disc space (the distance between the opposing end plates of the adjacent bones) must be restored. Restoring the appropriate height and orientation of the vertebral bones and the intervertebral space is critical, and when done properly (that is, through a series of sequentially larger trial spacers) is also instructive for the purposes of determining the appropriate size of the implant to be provided.

It shall be understood that the use of an anterior cervical plate in conjunction with the foregoing will be the preferred method of surgical treatment, however, its use should not be considered a requirement in the practice of the present invention, which should be viewed as a wholly separate and independent surgical process.

It is, therefore, an object of the present invention to provide a new and novel treatment for cervical disc pathology, as well as for the treatment of spinal pathologies in general.

It is, correspondingly, another object of the present invention to provide an intervertebral distraction tool that more accurately and easily separates collapsed intervertebral spaces and restores the proper anatomical orientation of cervical bones.

It is further an object of the present invention to provide an implantable intervertebral spacer device, and insertion instrument, which permits more anatomically appropriate and rapidly osteogenic fusion across the intervertebral space.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention, which provides an intervertebral distraction tool and an intervertebral spacer device and insertion instrument.

A preferred embodiment of an intervertebral distraction tool (also referred to herein as a trial) of the present invention has a proximal end defined by an elongate shaft, and a distal end defined by a clamshell head. The head has upper and lower halves, each having a curvate outer surface and a flat inner surface. The distal side of the head is hinged so that the head opens and closes from the proximal side of the head. Preferably, the hinge is a separating hinge that allows the halves to not only angulate with respect to one another about the hinge axis, but also to vertically separate from one another at the hinge. Preferably, the proximal side of the head has a tapered lip that facilitates insertion of the distal end of the distraction separator (described below) in between the halves. The head further has a pair of posts and corresponding bores into which the posts compress fit when the head is closed. The force of the compression fit holds the head closed, so that the head can be held closed during the insertion of the head into the target intervertebral space. When the distraction separator is actuated to open the head, the compression force is overcome to allow the head to open.

A preferred embodiment of a distraction separator of the present invention has an elongate shaft having a longitudinal bore. The distal end of the shaft has a decreasing taper defined by upper and lower surfaces that are angled toward one another, terminating at a distal face of the separator. The longitudinal bore accommodates the elongate shaft of the trial so that the separator can be moved longitudinally relative to the shaft. The longitudinal movement is preferably effected by simply pushing the proximal end of the separator toward the head of the trial. Upon forward movement of the separator, the tapered upper and lower surfaces engage the flat inner surfaces of the head, causing the halves to angulate about the hinge axis of the head, thereby opening the head. Further advancement of the separator in between the halves causes the halves to not only angulate with respect to one another about the hinge axis, but also to vertically separate from one another at the hinge, due to the separating hinge. Once the head has been opened as desired by the surgeon, extraction of the separator from between the halves and removal of the head from the intervertebral space leaves the distracted space ready for accepting additional trials or for insertion of a spacer of the present invention.

A preferred embodiment of a spacer device of the present invention has a thickness that is preferably predetermined to be a distance that is to be established between two vertebral discs that are to be fused together. The spacer further has an overall rectangular shape with rounded corners to limit interference with surrounding tissue during the insertion procedure. The spacer further has upper and lower surfaces that are curvate to allow them to more easily fit into and remain in the intervertebral space, with each curvate surface seating within the vertebral cavity presented to the surface when the spacer is disposed in the intervertebral space. The spacer is preferably formed from a material that can withstand compressive forces that are present within an intervertebral space, and further is preferably formed of a porous material that facilitates bone growth thereinto for a successful fusion procedure. Further preferably, the upper and lower surfaces are rough surfaces that will stimulate bone growth into the porous material. The spacer further has a plurality of linear grooves to facilitate insertion of the spacer into the intervertebral space. Each of the grooves has a depth, preferably is rounded, and preferably has a smooth surface.

A preferred embodiment of a spacer insertion tool of the present invention has a scissor-style body having upper and lower arms hinged about a hinge rod, each of the arms having a distal end having a head, each of the arms having a proximal end having a gripping handle. Each of the heads has an inner surface having a pair of linear protrusions that are spaced and dimensioned to fit within the linear grooves of the spacer when the heads are closed about the spacer. That is, when the arms are actuated by a surgeon gripping and bringing together the handles, the arms hinge about the hinge rod and therefore the heads are brought to bear on the spacer such that each of the protrusions fits into a respective one of the grooves, and the spacer is held between the heads by the continual compression of the spacer in this manner. Accordingly, the surgeon, while holding the spacer with the arms, can insert the spacer into the intervertebral space that has been distracted.

It should be noted that when the spacer is held with the arms, the upper and lower curvate surfaces are preferably not engaged by the heads. That is, the dimensions of the protrusions and/or the grooves are such that spaces are present between the upper and lower curvate surfaces and the inner surfaces of the heads. This feature is primarily provided so that when the spacer is released from the insertion tool, the upper and lower surfaces are not altered during the removal of the heads from the spacer.

In order to facilitate removal of the heads from the spacer so that the spacer can be left in the intervertebral space, the insertion tool is configured such that the arms can be moved longitudinally relative to a bracing rod. In the illustrated embodiment, this feature is provided in as much as the insertion tool is provided with a bore, preferably though the hinge rod, and the bracing rod is disposed through the bore.

In operation to remove the heads from the spacer while holding the spacer in the intervertebral space, the distal end of the bracing rod is held against the spacer by the surgeon while the surgeon pulls the handles. The pulling of the handles while the spacer is held in the intervertebral space causes the protrusions to slide out of the grooves until the spacer is released from the heads and is compressed between the vertebral discs by the natural compression force present in the spine. Accordingly, the upper and lower surfaces of the spacer, being curvate, easily fit into and remain in the intervertebral space, with each curvate surface seating within the vertebral cavity presented to the surface when the spacer is disposed in the intervertebral space. Further, the surfaces being rough, stimulate bone growth, and being porous, provide for bone growth into the material to facilitate fusion.

BRIEF DESCRIPTION OF THE DRAWINGS

FIGS. 2a-c show a distraction separator of the present invention in side, top and side views, respectively (with FIG. 2c showing the separator advanced within the trial of FIGS. 1a-c).

FIGS. 4a-b show a spacer insertion tool of the present invention in a side view and a front view, respectively, each showing the insertion tool holding the spacer of FIGS. 3a-c of the present invention, and the front view omitting the arms and handles of the insertion tool.

DETAILED DESCRIPTION

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions that follow are to be understood as illustrative and exemplary of specific structures, aspects and features within the broad scope of the present invention and not as limiting of such broad scope. Like numbers refer to similar features of like elements throughout.

Figure 1A:
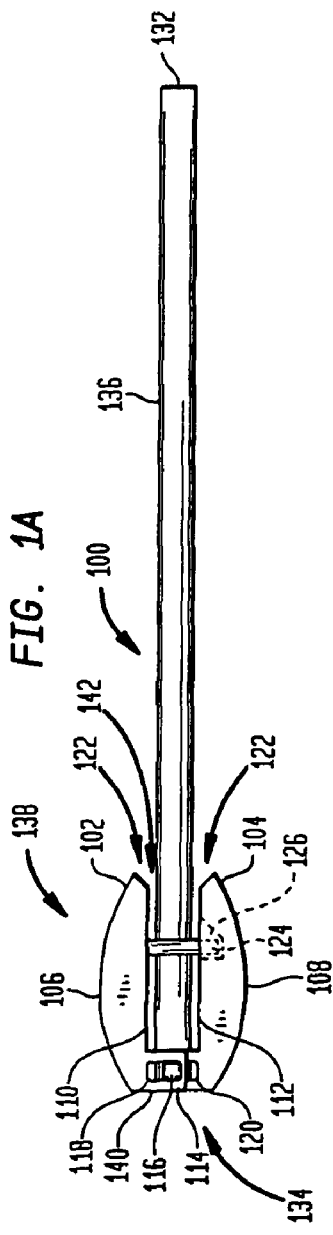
FIGS. 1a-c show an intervertebral distraction tool in two side views (FIG. 1a where the trial is closed, and FIG. 1b where the trial is open) and a top view, respectively.
Figure 1B:
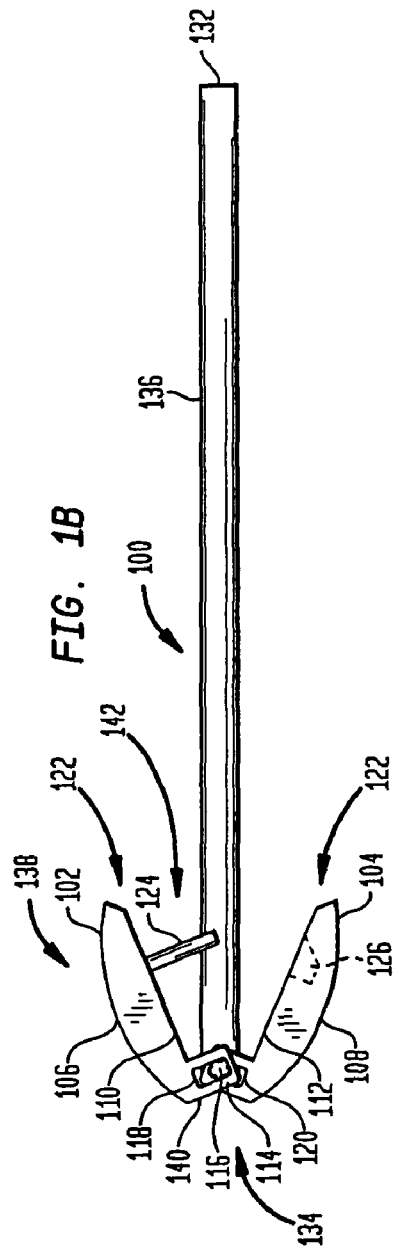
Figure 1C:
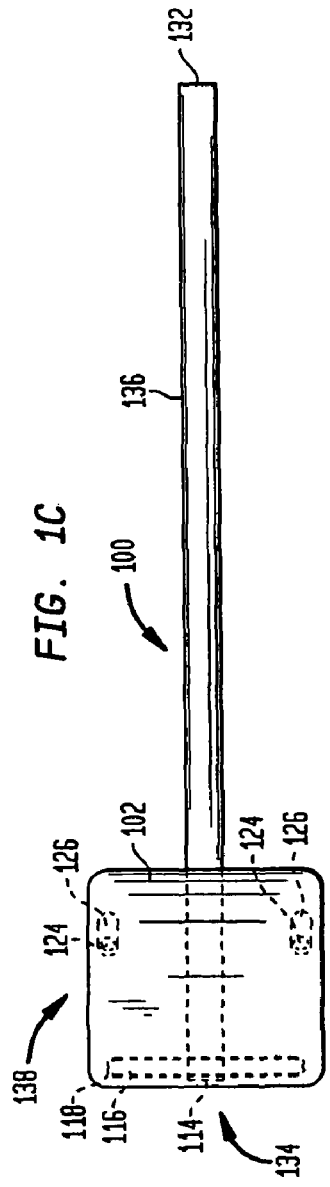

Referring now to FIGS. 1a-c, an intervertebral distraction tool 100 is shown in two side views (FIG. 1a where the trial 100 is closed, and FIG. 1b where the trial 100 is open) and a top view, respectively. The trial 100 has a proximal end 132 and a distal end 134, the proximal end 132 being defined by an elongate shaft 136, and the distal end 134 being defined by a clamshell head 138. The head 138 has an overall rectangular shape with rounded corners to limit interference with surrounding tissue during the distraction procedure. It should be understood that the shape of the head 138 can be any shape that fits between vertebral bodies, that other embodiments of the present invention may not use rectangular shaped heads. Further, other embodiments of the present invention may or may not have rounded corners on the head 138, depending on the clinical necessity or desirability of such or similar features.

The head 138 has upper 102 and lower 104 halves, each having a curvate outer surface 106, 108 and a flat inner surface 110, 112. As will be described below, the curvature of the outer surfaces 106, 108 facilitates the distraction of the vertebral bodies, but it should be understood that the curvature is not necessary for the functioning of the present invention, and that outer surfaces of alternate conformity can be used without departing from the scope of the present invention. Similarly, the flat contour of the inner surfaces 110, 112 is preferred, but other contours can be provided within the scope of the present invention.

The distal side 140 of the head 138 is hinged so that the head 138 opens and closes from the proximal side 142 of the head 138. Preferably, as shown, the hinge 114 is a separating hinge that allows the halves 102, 104 to not only angulate with respect to one another about the hinge axis, but also to vertically separate from one another at the hinge. This is achieved by the use of a hinge pin 116 having a diameter smaller than the height of the each half's hinge bore 118, 120. It should be understood that the use of a separating hinge is not necessary for the functioning of the present invention, but rather is preferred, and that nonseparating hinges, and other mechanisms that allow the halves to angulate with respect to one another (with or without separating vertically) can be provided within the scope of the present invention.

Preferably, as shown, the proximal side 142 of the head 138 has a tapered lip 122 that facilitates insertion of the distal end of the distraction separator (described below) in between the halves 102, 104 (best shown in FIG. 2c, described below). The head 138 further has a pair of posts 124 and corresponding bores 126 into which the posts 124 compress fit when the head 138 is closed. The force of the compression fit holds the head 138 closed, so that the head 138 can be held closed during the insertion of the head 138 into the target intervertebral space (the space into which the spacer of the present invention, described below, will be placed to facilitate fusion of the adjacent vertebral bodies). When the distraction separator (described below) is actuated to open the head 138, the compression force is overcome to allow the head 138 to open. It should be understood that the post and bore configuration is preferable, but that other mechanisms can be provided to hold the head 138 closed, without departing from the scope of the present invention.

Referring now to FIGS. 2a-c, a distraction separator 200 of the present invention is shown in side, top and side views, respectively (with FIG. 2c showing the separator 200 advanced within the trial 100 described above). The separator 200 has an elongate shaft 202 having a longitudinal bore 208 and a proximal end 204 and a distal end 206. The distal end 206 has a decreasing taper defined by upper 210 and lower 212 surfaces that are angled toward one another, terminating at a distal face 214 of the separator 200. The longitudinal bore 208 accommodates the elongate shaft 136 of the trial 100 so that the separator 200 can be moved longitudinally relative to the shaft 136. The longitudinal movement is preferably effected by simply pushing the proximal end 204 toward the head 138. However, it should be noted that other mechanisms for moving the separator 200 can be used, including, but not limited to, for example, providing threads on the walls of the longitudinal bore 208, corresponding threads on the outer surface of the shaft 136, and providing for rotational movement of the threaded portions of the shaft 136 relative to the distal end 134 of the shaft 136, so that rotation of the shaft 136 causes forward movement of the separator 200 relative to the shaft 136 and reverse rotation of the shaft 136 causes backward movement of the separator 200 relative to the shaft 136.

As best shown in FIG. 2c, upon forward movement of the separator 200, the tapered upper and lower surfaces 210, 212 engage the flat inner surfaces 110, 112 of the head 138, causing the halves 102, 104 to angulate about the hinge axis of the head 138, thereby opening the head 138. The further the separator 200 is advanced in between the halves 102, 104, the further the head 138 opens. Therefore, the surgeon can vary the amount of distraction. In addition, further advancement of the separator 200 in between the halves 102, 104 causes the halves 102, 104 to not only angulate with respect to one another about the hinge axis, but also to vertically separate from one another at the hinge, due to the separating hinge 114. Once the head 138 has been opened as desired by the surgeon, extraction of the separator 200 from between the halves 102, 104 (preferably by simply pulling on the proximal end 204, but alternatively by other mechanisms, as described above) and removal of the head 138 from the intervertebral space leaves the distracted space ready for accepting additional trials (for example, thicker trials and/or trials that open to greater distances) or for insertion of a spacer of the present invention (described below). With regard to accepting additional trials, it should be noted that a plurality of trials can be provided, each having an individually unique thickness and/or an individually unique distance to which the head of the trial can be opened. Therefore, the surgeon can distract the space to any desired distance through the use of one or more of such trials.

Figure 3A:
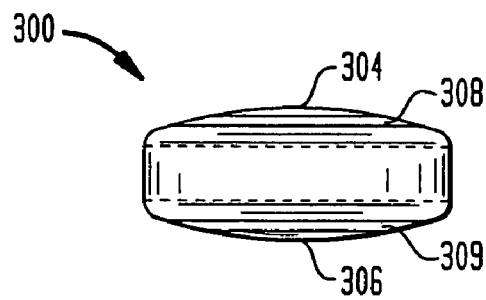
FIGS. 3a-c show a spacer device of the present invention in side, front and top views, respectively.
Figure 3B:
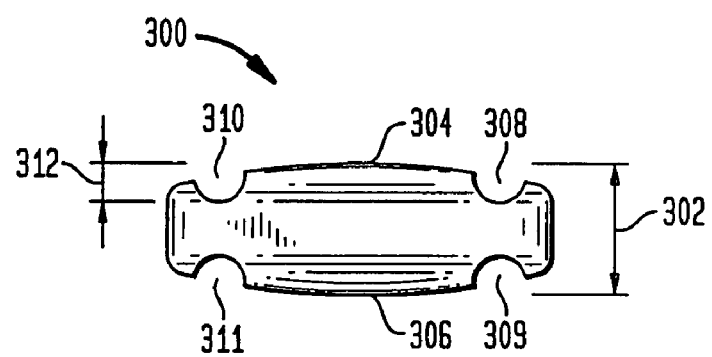
Figure 3C:
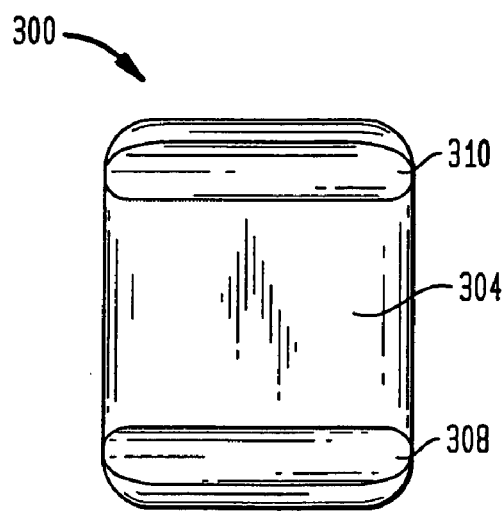

With regard to inserting spacers, and referring now to FIGS. 3a-c, a spacer 300 of the present invention is shown in side, front and top views, respectively. The spacer 300 has a thickness 302 that is preferably predetermined to be a distance that is to be established between two vertebral discs that are to be fused together. The spacer 300 further has an overall rectangular shape with rounded corners and edges to limit interference with surrounding tissue during the insertion procedure. It should be understood that the shape of the spacer 300 can be any shape that fits between vertebral bodies, that other embodiments of the present invention may not use rectangular shaped heads. Further, other embodiments of the present invention may or may not have rounded corners or edges on the spacer 300, depending on the clinical necessity or desirability of such or similar features.

The spacer 300 further has upper and lower surfaces 304, 306 that are curvate to allow them to more easily fit into and remain in the intervertebral space, with each curate surface 304, 306 seating within the vertebral cavity presented to the surface when the spacer 300 is disposed in the intervertebral space. These surfaces give the spacer 300 a shape similar to a pillow. It should be understood that the curvature is preferable but not necessary for the functioning of the present invention, and that surfaces of alternate conformity can be used without departing from the scope of the present invention.

The spacer 300 is preferably formed from a material that can withstand compressive forces that are present within an intervertebral space, and further is preferably formed of a porous material that facilitates bone growth thereinto for a successful fusion procedure. Examples of materials suitable for this purpose include porous metals and compacted wire meshes, bone morphogenic protein, and polylactic lactic acid. Further preferably, the upper and lower surfaces 304, 306 are rough surfaces that will stimulate bone growth into the porous material.

The spacer 300 further has a plurality of linear grooves 308, 309, 310, 311 to facilitate insertion of the spacer 300 into the intervertebral space (as described below). For reasons explained in greater detail below, each of the grooves has a depth 312, preferably is rounded, and preferably has a smooth surface. It should be noted that although two grooves are shown on each upper and lower surface of the spacer, more or fewer grooves can be used without departing from the scope of the present invention.

It should be understood that a plurality of spacers 300 of the present invention can be provided, having individually unique thicknesses. Preferably, the thicknesses are predetermined to be distances that are to be established between two vertebral discs that are to be fused together. That is, depending on the clinical application, the intervertebral space may be distracted to a particular distance (e.g., by the distraction process described above), and a plurality of spacers can be provided with different thicknesses so that at least one has a thickness matching the particular intervertebral distance in any given clinical application. Preferably, each of the plurality of spacers has linear grooves that preferably are of the same depth 312 from spacer to spacer (so that if desired a single insertion tool (e.g., of a type described below) can be used to insert more than one of the spacers), preferably are rounded, and preferably have smooth surfaces.

Referring now to FIGS. 4a-b, a spacer insertion tool 400 of the present invention is shown in a side view and a front view, respectively, each showing the insertion tool 400 holding the spacer 300 of the present invention, and the front view omitting the arms and handles of the insertion tool. The insertion tool 400 has a scissor-style body 402 having upper 404 and lower 406 arms hinged about a hinge rod 408, each of the arms 404, 406 having a distal end 410, 412 having a head 414, 416, each of the arms 404, 406 having a proximal end 418, 420 having a gripping handle 422, 424. It should be noted that while the insertion tool 400 of the illustrated embodiment has a scissor-style body 402 to open and close the heads 414, 416, other embodiments of the present invention may have bodies of other styles that may or may not utilize hinges or similar structures to open and close the heads 414, 416.

Each of the heads 414, 416 has an inner surface 426, 428 having a pair of linear protrusions 430, 432, 434, 436 that are spaced and dimensioned to fit within the linear grooves 308, 309, 310, 311 of the spacer 300 when the heads 414, 416 are closed about the spacer 300. (As noted above, although two grooves are shown on each upper and lower surface of the spacer, more or fewer grooves can be used without departing from the scope of the present invention, and hence more or fewer corresponding protrusions can be used on the heads 414, 416 without departing from the scope of the present invention; it should also be noted that it is not necessary for the number of grooves to equal the number of protrusions.) That is, when the arms 404, 406 are actuated by a surgeon gripping and bringing together the handles 422, 424, the arms 404, 406 hinge about the hinge rod 408 and therefore the heads 414, 416 are brought to bear on the spacer 300 such that each of the protrusions 430, 432, 434, 436 fits into a respective one of the grooves 308, 309, 310, 311, and the spacer 300 is held between the heads 414, 416 by the continual compression of the spacer 300 in this manner. Accordingly, the surgeon, while holding the spacer 300 with the arms 404, 406, can insert the spacer 300 into the intervertebral space that has been distracted (e.g., according to the procedures described above).

It should be noted that when the spacer 300 is held with the arms 404, 406, the upper and lower curvate surfaces 304, 306 are preferably not engaged by the heads 414, 416. That is, the dimensions of the protrusions 430, 432, 434, 436 and/or the grooves 308, 309, 310, 311 are such that spaces 438, 440 are present between the upper and lower curvate surfaces 304, 306 and the inner surfaces 426, 428 of the heads 414, 416. This feature is primarily provided so that when the spacer 300 is released from the insertion tool 400 (as described below), the upper and lower surfaces 304, 306 (preferably being rough and porous as noted above) are not altered during the removal of the heads 414, 416 from the spacer 300. During the removal, the heads 414, 416 only engage the spacer 300 at the grooves 308, 309, 310, 311, and therefore the upper and lower surfaces 304, 306 are not at risk for being damaged.

In order to facilitate removal of the heads 414, 416 from the spacer 300 so that the spacer 300 can be left in the intervertebral space, the insertion tool 400 is configured such that the arms 404, 406 can be moved longitudinally relative to a bracing rod 444. In the illustrated embodiment, this feature is provided inasmuch as the insertion tool is provided with a bore 442, preferably though the hinge rod 408 as shown, and the bracing rod 444 that is disposed through the bore 442. It should be understood that other embodiments may use other configurations to effect the same or similar functionality.

The longitudinal movement of the arms 404, 406 relative to the bracing rod 444 is preferably effected by holding the bracing rod 444 and pulling the handles 422, 424. The bracing rod 444 has a proximal end 446 and a distal end 448. In operation to remove the heads 414, 416 from the spacer 300 while holding the spacer 300 in the intervertebral space, the distal end 448 of the bracing rod 444 is held against the spacer 300 by the surgeon (e.g., by gripping and maintaining the position of the proximal end) while the surgeon pulls the handles 422, 424. The pulling of the handles 422, 424 while the spacer 300 is held in the intervertebral space causes the protrusions 430, 432, 424, 436 to slide out of the grooves 308, 309, 310, 311 (the grooves and the protrusions are preferably rounded and smoothed as noted above to facilitate this sliding) until the spacer 300 is released from the heads 414, 416 and is compressed between the vertebral discs by the natural compression force present in the spine. Accordingly, the upper and lower surfaces 304, 306 of the spacer 300, being curvate, easily fit into and remain in the intervertebral space, with each curvate surface 304, 306 seating within the vertebral cavity presented to the surface when the spacer 300 is disposed in the intervertebral space. Further, the surfaces 304, 306 being rough, stimulate bone growth, and being porous, provide for bone growth into the material to facilitate fusion.

It should be noted that other mechanisms for moving the arms 404, 406 relative to the bracing rod 444 can be used, including, but not limited to, for example, providing threads on the walls of the bore 442, corresponding threads on the outer surface of the bracing rod 444, and providing for rotational movement of the threaded portion of the bracing rod 444 relative to the distal end 448 of the bracing rod 444, so that rotation of the bracing rod 444 causes forward movement of the arms 404, 406 relative to the bracing rod 414 and reverse rotation of the bracing rod 444 causes backward movement of the arms 404, 406 relative to the bracing rod 444.

It should also be noted that if desired, a plurality of insertion tools 400 can be provided for inserting a plurality of spacers 300, where the spacers 300 are of different thicknesses and the insertion tools 400 open to different distances, so that one or more insertion tools 400 can be used to more effectively grip a particular spacer or set of spacers 300.

While there has been described and illustrated specific embodiments of the present invention, it will be apparent to those skilled in the art that variations and modifications are possible without deviating from the broad spirit and principle of the present invention. The invention, therefore, shall not be limited to the specific embodiments discussed herein.

The invention claimed is:

1. A method of distracting vertebral bodies comprising:
providing a distraction tool including a longitudinal shaft having a distal end and a proximal end, a trial head pivotally connected by a hinge on the distal end of the longitudinal shaft and at least partially extending from the hinge in a proximal direction towards the proximal end of the longitudinal shaft, the shaft extending proximal of a proximal end of the trial head, and a head separator having an engagement portion;
inserting the trial head between the vertebral bodies; and
moving the head separator with respect to the longitudinal shaft and the engagement portion into engagement with the trial head, thereby pivoting and separating first and second portions of the trial head at least the hinge.

2. The method of claim 1, wherein the first and second portions of the trial head are pivotally connected with the longitudinal shaft, the separating step including pivoting of the first and second portions.

3. The method of claim 2, wherein the separating step includes laterally separating the first and second portions.

4. The method of claim 1, wherein the moving step includes longitudinally moving the head separator with respect to the longitudinal shaft.

5. The method of claim 4, wherein the moving step includes longitudinally moving the head separator over the longitudinal shaft.

6. The method of claim 1, wherein the first and second portions each have a distal end and a proximal end, the distal ends of the first and second portions being hinged to one another at the hinge on the distal end of the longitudinal shaft so that the proximal ends of the first and second portions are openable and closeable about the longitudinal shaft.

7. The method of claim 1, wherein each of the first and second portions has a curvate outer surface and a flat inner surface.

8. The method of claim 1, wherein proximal ends of the first and second portions are laterally inwardly tapered toward the distal end of the longitudinal shaft and the engagement portion of the head separator is laterally inwardly tapered toward the distal end of the longitudinal shaft, so that when the engagement portion engages the proximal ends of the first and second portions, the inwardly tapered portion of the engagement portion pushes the inwardly tapered portions of the first and second portions laterally away from the longitudinal shaft.

9. The method of claim 8, wherein the head separator comprises a longitudinal sleeve having a longitudinal bore through which the longitudinal shaft is disposed so that the longitudinal sleeve is longitudinally translatable on the longitudinal shaft, the longitudinal sleeve having a distal end that includes the engagement portion.

10. A method of distracting vertebral bodies comprising:
providing a distraction tool including:
a longitudinal shaft having a distal end and a proximal end;
a trial head having first and second portions pivotally connected by a hinge on the distal end of the longitudinal shaft and at least partially extending from the hinge in a proximal direction towards the proximal end of the longitudinal shaft, the shaft extending proximal of a proximal end of the trial head; and
a head separator having an engagement portion;
inserting the trial head between the vertebral bodies;
moving the head separator with respect to the longitudinal shaft and the engagement portion into engagement with the trial head, thereby pivoting and separating first and second portions of the trial head at least the hinge; and
removing the trial head from between the vertebral bodies.

11. The method of claim 10, wherein the separating step includes laterally separating the first and second portions.

12. The method of claim 10, wherein the moving step includes longitudinally moving the head separator with respect to the longitudinal shaft.

13. The method of claim 12, wherein the moving step includes longitudinally moving the head separator over the longitudinal shaft.

14. The method of claim 10, wherein the first and second portions each have a distal end and a proximal end, the distal ends of the first and second portions being hinged to one another so that the proximal ends of the first and second portions are openable and closeable about the longitudinal shaft.

15. The method of claim 10, wherein each of the first and second portions has a curvate outer surface and a flat inner surface.

16. The method of claim 10, wherein proximal ends of the first and second portions are laterally inwardly tapered toward the distal end of the longitudinal shaft and the engagement portion of the head separator is laterally inwardly tapered toward the distal end of the longitudinal shaft, so that when the engagement portion engages the proximal ends of the first and second portions, the inwardly tapered portion of the engagement portion pushes the inwardly tapered portions of the first and second portions laterally away from the longitudinal shaft.

17. The method of claim 16, wherein the head separator comprises a longitudinal sleeve having a longitudinal bore through which the longitudinal shaft is disposed so that the longitudinal sleeve is longitudinally translatable on the longitudinal shaft, the longitudinal sleeve having a distal end that includes the engagement portion.

18. A method of distracting vertebral bodies comprising:
providing a distraction tool including:
a longitudinal shaft having a distal end and a proximal end,
a trial head having first and second portions pivotally hinged by a hinge that allows the first and second portions to angulate with respect to one another at the hinge and that allows the first and second portions to separate from one another at the hinge, the first and second portions connected at the distal end of the longitudinal shaft and at least partially extending towards the proximal end of the longitudinal shaft, and
a head separator having an engagement portion, the head separator having a longitudinal sleeve with a longitudinal bore through which the longitudinal shaft is disposed so that the longitudinal sleeve is longitudinally translatable on the longitudinal shaft, the longitudinal sleeve having a distal end that includes the engagement portion;
wherein proximal ends of the first and second portions are laterally inwardly tapered toward the distal end of the longitudinal shaft and the engagement portion of the head separator is laterally inwardly tapered toward the distal end of the longitudinal shaft, so that when the engagement portion engages the proximal ends of the first and second portions, the inwardly tapered portion of the engagement portion pushes the inwardly tapered portions of the first and second portions laterally away from the longitudinal shaft;
inserting the trial head between the vertebral bodies;

moving the head separator with respect to the longitudinal shaft and the engagement portion into engagement with the trial head, thereby causing the first and second portions to angulate with respect to one another at the hinge and causing distal ends of the first and second portions to separate from one another at the hinge separating first and second portions of the trial head; and removing the trial head from between the vertebral bodies.

* * * * *